United States Patent

Blümel et al.

[11] Patent Number: 4,742,808
[45] Date of Patent: May 10, 1988

[54] METHOD AND SYSTEM FOR RECOGNIZING THE READINESS FOR OPERATION OF AN OXYGEN MEASUREMENT SENSOR

[75] Inventors: Thomas Blümel, Schmitten; Harald Collonia, Beselich-Schupach, both of Fed. Rep. of Germany

[73] Assignee: VDO Adolf Schindling AG, Frankfurt am Main, Fed. Rep. of Germany

[21] Appl. No.: 86,100

[22] Filed: Aug. 14, 1987

[30] Foreign Application Priority Data

Aug. 23, 1986 [DE] Fed. Rep. of Germany ....... 3628707
Nov. 3, 1986 [DE] Fed. Rep. of Germany ....... 3637304

[51] Int. Cl.⁴ .................... F02M 51/00; F02D 41/14; G01N 27/50
[52] U.S. Cl. .................................. 123/489; 204/425; 204/426; 123/440
[58] Field of Search ............................ 123/440, 489, ; 204/424, 425, 426, 427, 428, 429

[56] References Cited

U.S. PATENT DOCUMENTS

| | | | |
|---|---|---|---|
| 4,472,262 | 9/1984 | Kondo et al. | 204/426 X |
| 4,543,176 | 9/1985 | Harada et al. | 204/425 X |
| 4,561,402 | 12/1985 | Nakano et al. | 123/489 |
| 4,609,452 | 9/1986 | Shimomura | 204/426 X |
| 4,609,453 | 9/1986 | Shimomura | 204/426 X |
| 4,626,338 | 12/1986 | Kondo et al. | 204/426 X |

Primary Examiner—Willis R. Wolfe
Attorney, Agent, or Firm—Martin A. Farber

[57] ABSTRACT

A method for detecting the readiness for operation of an oxygen measurement sensor which is located in the exhaust pipe of an internal combustion engine and serves, together with a regulating device, to regulate the preparation of the mixture for the internal combustion engine. The voltage present at the oxygen measurement sensor is measured in succession for two different conditions of load and the internal resistance is calculated from the results of the measurement and compared with a predetermined value.

14 Claims, 2 Drawing Sheets

METHOD AND SYSTEM FOR RECOGNIZING THE READINESS FOR OPERATION OF AN OXYGEN MEASUREMENT SENSOR

FIELD AND BACKGROUND OF THE INVENTION

The invention relates to a method and system for recognizing the readiness for operation of an oxygen measurement sensor which is located in the exhaust pipe of an internal combustion engine and, together with a regulating device, serves to regulate the preparation of the mixture for the internal combustion engine.

In order to obtain exhaust gasses which are as free of injurious substances as possible, regulating devices for internal combustion engines are known in which the oxygen content in the exhaust pipe is measured and evaluated. For this purpose, oxygen measurement sensors, so-called lambda sensors, are known which operate in accordance with the principle of ion conduction through a solid electrolyte as a result of a difference in oxygen partial-pressure and give off, corresponding to the oxygen partial-pressure present in the exhaust gas, a voltage signal which exhibits a jump in voltage upon transition from an oxygen deficiency to an excess of oxygen.

The internal resistance of the known oxygen measurement sensors is, however, so large at low temperatures that the signal given off by the oxygen measurement sensor upon a cold start and during the warming-up phase of the internal combustion engine cannot be evaluated. In known devices for regulating the preparation of the mixture, a control which is independent of the output signal of the oxygen measurement sensor is therefore provided up to the region of readiness for operation of the oxygen measurement sensor. Only when the oxygen measurement sensor has reached its readiness for operation is its output signal used to regulate the fuel/air ratio.

In one known method of monitoring the readiness for operation of an oxygen measurement sensor, the oxygen measurement sensor is acted on by a test voltage having a constant mean value of the voltage which can be produced by the oxygen measurement sensor. The resultant voltage at the output of the sensor is fed as control variable of the readiness for operation to two comparison devices for comparison with an upper sensor value and a lower sensor value, in each case corresponding to a minimum output voltage of the oxygen measurement sensor, and via a timing element, a mixture control device is connected or disconnected instead of the mixture regulating device corresponding to the output signal of the comparison device.

In another known method of monitoring the readiness for operation of an oxygen measurement sensor in which a voltage resulting under the influence of the behavior of the sensor is also detected by two comparison circuits with threshold voltages and then evaluated, a constant reference voltage is connected in opposition for the detection of the sensor internal resistance of the oxygen measurement sensor which characterizes the readiness for operation of the sensor, in which connection the threshold voltages of the comparison circuits, which voltages are connected in opposition to the output voltage resulting therefrom, lie above and below the reference voltage by predetermined difference values, and in this connection the output signals from a subsequent evaluation circuit which are given off by the comparison circuits and correspond to a total of three logical states of switching, are processed for switching from regulation to control and vice versa.

SUMMARY OF THE INVENTION

It is an object of the present invention to provide a method of recognizing the readiness for operation of an oxygen measurement sensor which can be carried out in reliable manner with simple and economical means. Furthermore, it is to be possible, through the invention, to adapt the recognition by simple means to the conditions present at the time.

According to the method of the invention, the voltage present on the oxygen measurement sensor is measured in succession for two different conditions of load and the internal resistance is calculated from the measurement results and compared with a pre-determined value.

The method of the invention can be used not only for monitoring the oxygen measurement sensor during the warming-up phase but also for monitoring during operation.

By the method of the invention an exact measurement of the internal resistance is obtained. By the subsequent comparison with the predetermined value, a clear criterion as to readiness for operation is given. The predetermined value can be easily adapted in particular to the conditions in the individual case if the predetermined value, in accordance with another feature of the invention, is deposited in (removed from) a memory the content of which is variable.

In accordance with another further development of the invention, the different conditions of load are obtained in the manner that a series connection of the oxygen measurement sensor and a resistor is acted on alternately by two different voltages.

In this connection, one advantageous embodiment resides in the fact that the one voltage is 0 volts and the other voltage is a reference voltage.

The reference voltage is, furthermore, preferably fed to an analog/digital converter.

One advantageous arrangement for the carrying out of the method of the invention resides therein that a first terminal of the oxygen measurement sensor (1) is connected to constant potential and a second terminal is connected by resistor (13) to a source of voltage (6–11) that can be switched by a microcomputer (5), and that furthermore, the input of an analog/digital converter (4) which is associated with the microcomputer (5) is connected to the second terminal.

With suitable programming, a microcomputer which is in any event used for regulating purposes can be used to carry out the method of the invention by merely adding a few more electronic elements.

The microcomputers with integrated analog/digital converter at present available on the market have input resistances which are no greater than that of the oxygen measurement sensor in the cold. In order to make it possible to use these commercially available microcomputers, it is necessary, in accordance with a further development of the invention, that an impedance-converter (3) be arranged between the second terminal of the oxygen measurement sensor (1) and the input of the analog/digital converter (4).

One particularly simple embodiment of the arrangement for the carrying out of the method of the invention provides that the switchable voltage source (6–11) comprises essentially a transistor (9) whose emitter terminal is connected to a terminal of a source of constant voltage, and a collector resistor (10) connected between a collector terminal of the transistor and a terminal of the source of voltage (11).

In a further embodiment of the invention, the different conditions of load are obtained in the manner that the oxygen measurement sensor or probe is alternately acted on by a first resistor and a parallel circuit consisting of the first and a second resistor. In this way, simple circuits are possible for the carrying out of the method.

The pre-determined value can be particularly easily adapted to the conditions of the individual case if it is taken, in accordance with a further development of the method of the invention, from a memory the content of which is variable.

One advantageous circuit for the carrying out of the method of the invention is characterized by the fact that the oxygen measurement sensor (1), a first resistor (31) and a series circuit of a second resistor (30) and a switch (29) controllable by a microcomputer (25) are connected in parallel and that furthermore the input (23) of an analog-to-digital converter (24) which is associated with the microcomputer (25) is connected to the oxygen measurement sensor (1).

In accordance with a further development an impedance-transformer (22) is arranged between the second terminal of the oxygen measurement probe (1) and the input (23) of the analog-to-digital converter (24).

A particularly simple embodiment of the circuit for the carrying out of the method of the invention is that the controllable switch (29) comprises essentially a transistor.

BRIEF DESCRIPTION OF THE DRAWINGS

With the above and other objects and advantages in view, the present invention will become more clearly understood in connection with the detailed descriptions of preferred embodiments when considered with the accompanying drawings, of which.

DETAILED DESCRIPTION OF THE PREFERRED EMBODIMENTS

Figure 1:
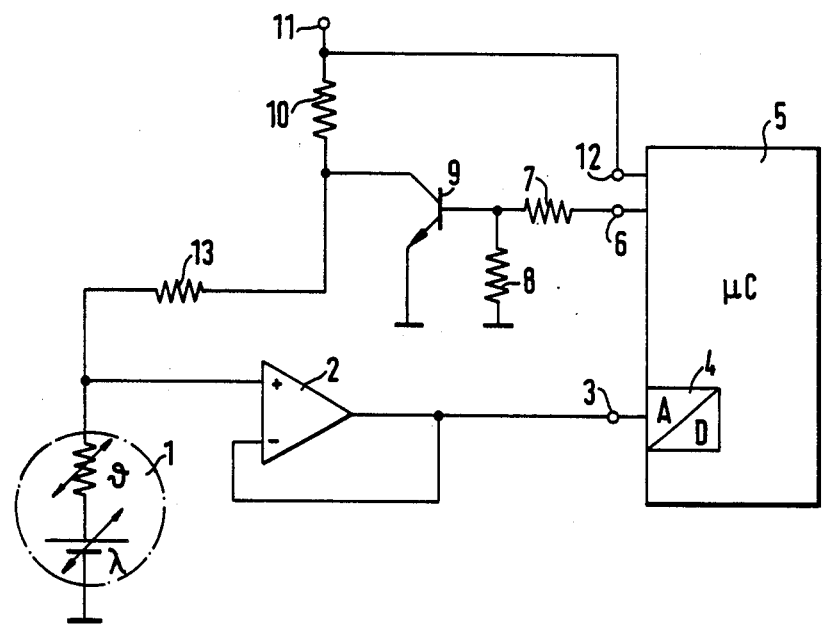
FIGS. 1 and 2 show alternative circuit diagrams of the invention.

The known oxygen measurement sensor 1 is represented in the figure merely by a source of voltage, the voltage of which is dependent on the percentage of oxygen and the internal resistance Ri of which is temperature-dependent. The output voltage of the oxygen measurement sensor is fed via an operational amplifier 2 connected as impedance-converter to an input 3 of an analog/digital converter 4 which is part of a microcomputer 5. The base of a transistor 9 is connected to one output 6 of the microcomputer via a voltage divider comprising resistors 7, 8. The emitter of the transistor 9 is connected to ground potential, while the collector of the transistor 9 is connected via a collector resistor 10 to a terminal 11 of a source of voltage which also serves as reference voltage for the analog/digital converter 4 and is therefore connected to another input 12 of the microcomputer 5. The oxygen measurement sensor 1 is furthermore connected via resistor 13 to the collector of the transistor 9.

By means of a program which is stored in the microcomputer 5, the transistor 9 is now alternately switched to non-conductive and conductive state in order to determine the readiness for operation of the oxygen measurement sensor. If the transistor 9 is non-conductive, then the series connection consisting of the oxygen measurement sensor 1 and the resistor 13 is acted on by a voltage which is equal approximately to the reference voltage fed at 11 since the value of the resistor 10 is substantially less than the value of the resistor 13.

The resistor 13 is so dimensioned that, on the one hand, it permits a reliable measurement of the internal resistance of the oxygen measurement sensor 1 and, on the other hand, does not cause any substantial falsification of the sensor signal upon the evaluation of the sensor signal in the state of readiness for operation. In the oxygen measurement sensors customarily used, the internal resistance in cold condition is about 15 Mohm, while in operating condition it is about 10 kohm or less. For the value of the resistor 13, a value of about 1 Mohm has proven favorable, at which, on the one hand, a reliable measurement of the internal resistance before readiness for operation is present and on the other hand, no noticeable falsification of the output signal of the oxygen measurement sensor is present. Furthermore, by a resistor 13 of this value, the oxygen measurement probe is not loaded above its permissable tolerances.

If the transistor is conductive, then the oxygen measurement probe is loaded by the resistor 13. By measuring the voltage at the oxygen measurement sensor 1, the internal resistance can easily be calculated in both cases with the aid of the microcomputer in accordance with the equation $$R_i = R_L \frac{V_H - V_L}{V_{ref} - V_H + V_L}$$

This value is then compared with a stored value. If the value found is less than the stored value, then the voltage given off by the oxygen measurement sensor 1 and fed by the impedance converter 2 to the analog/digital converter 4 is used to regulate the preparation of the mixture by means of the microcomputer 5.

Figure 2:
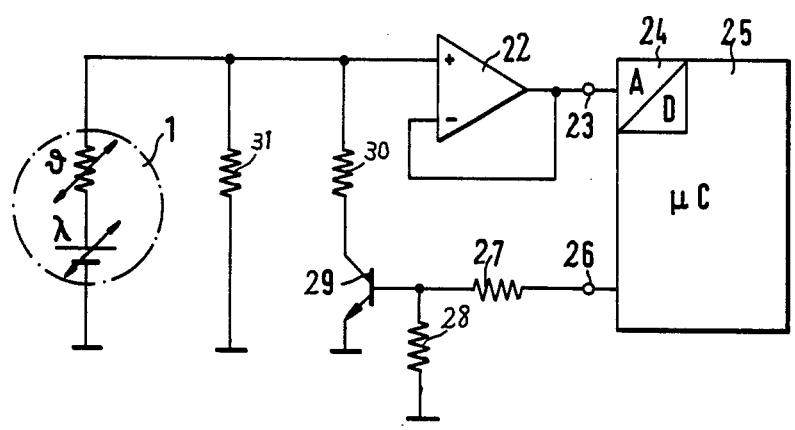

With reference to FIG. 2, there is described an alternative embodiment of the invention. The known oxygen measurement sensor 1 is shown in the Figure merely as a source of voltage, the voltage of which is dependent on the percentage of oxygen and the internal resistance $R_i$ of which is dependent on temperature. The output voltage of the oxygen measurement sensor 1 is fed, via an operational amplifier 22 connected as impedance-transformer, to an input 23 of an analog-to-digital converter 24 which is part of a microcomputer 25. The base of a transistor (switch) 29 is connected to an output 26 of the microcomputer via a voltage divider comprising resistors 27, 28. The emitter of the transistor 29 is connected to ground potential while the collector of the transistor 29 is connected via a resistor 30 to the oxygen measurement sensor. Another resistor 31 is furthermore connected to the oxygen measurement sensor 1.

By a program stored in the microcomputer 25 the transistor 29 is now controlled alternately into non-conductive and conductive state so as to recognize the readiness for operation of the oxygen measurement sensor. If the transistor 29 is non-conductive then the oxygen measurement sensor 1 is acted on merely by the resistor 31. If the transistor 29 is conductive, then loading by the parallel circuit of both resistors is present. From the ratio of the output voltages of the oxygen measurement sensor 1 with the two loads, the internal resistance $R_i$ is calculated. The measurement is sufficiently rapid that the output voltage remains practically unchanged during a measurement cycle.

The resistors 30 and 31 are so dimensioned that, on the one hand, a reliable measurement of the internal resistance of the oxygen measurement sensor 1 is made possible and, on the other hand, no substantial falsification of the sensor signal is brought about in the condition of readiness for operation upon the evaluation of the sensor signal. As noted above, with the oxygen measurement sensors customarily used, the internal resistance in cold state amounts to about 15 Mohm while in operating condition it is about 10 kohm or less. Therefore, there has proven favorable for the resistors 30 and 31 to have a value of about 1 Mohm at which, on the one hand, a dependable measurement of the internal resistance before the readiness for operation is present and, on the other hand, no perceptible falsification of the output signal of the oxygen measurement sensor exists.

The value found for the internal resistance is then compared with a stored value. If the value found is less than the value stored then the voltage given off by the oxygen measurement sensor 1 and fed via the impedance transformer 22 to the analog-to-digital converter 24 is used to regulate the preparation of the mixture by means of the microcomputer 25.

We claim:

1. A method for recognizing the readiness for operation of an oxygen measurement sensor which is located in an exhaust pipe of an internal combustion engine and, together with a regulating device, serves to regulate the preparation of a fuel-air mixture for the internal combustion engine, comprising the steps of
    measuring the voltage present in the oxygen measurement sensor in succession for two different conditions of load,
    calculating the internal resistance from the measurement results; and
    comparing the calculated internal resistance with a predetermined value.
2. The method according to claim 1, wherein said measuring step includes
    connecting said sensor in series with a resistor; and
    obtaining the different conditions of load by alternately applying two different voltages on the series connection of the oxygen measurement sensor and the resistor.
3. The method according to claim 2, wherein said step of calculating includes
    extracting the predetermined value from a memory, the latter having a variable content.
4. The method according to claim 3, wherein one voltage is 0 volts and the other voltage is a reference voltage.
5. The method according to claim 4, further comprising the step of
    feeding the reference voltage to an analog/digital converter.
6. A system connectable to a fixed source of voltage having a first terminal and a second terminal for determining a state of readiness for operation of an oxygen measurement sensor, comprising
    an oxygen measurement sensor having a first terminal and a second terminal;
    a resistor;
    a switchable voltage source energizable by the fixed voltage source, said first sensor terminal being connectable to the first terminal of said fixed source of voltage, said second sensor terminal being connected via said resistor to said switchable voltage source;
    a microcomputer for operating said switchable voltage source to switch between levels of voltage; and
    an analog/digital converter connected between said second sensor terminal and said computer for inputting a voltage thereto.
7. The system according to claim 6, further comprising
    an impedance-converter connected between the second terminal of the oxygen measurement sensor and an input of the analog/digital converter.
8. The system according to claim 7, wherein the switchable voltage source comprises
    a transistor having an emitter terminal connected to the first terminal of said voltage source; and
    a collector resistor connecting between a collector terminal of said transistor and the second terminal of said fixed voltage source.
9. The system according to claim 6, wherein the switchable voltage source comprises
    a transistor having an emitter terminal connected to the first terminal of said voltage source; and
    a collector resistor connecting between a collector terminal of said transistor and the second terminal of said fixed voltage source.
10. The method according to claim 1, further comprising
    obtaining the different conditions of load by alternately connecting to the oxygen measurement sensor a first resistor and a parallel circuit comprising the first resistor and a second resistor.
11. The method according to claim 10, wherein the predetermined valve is taken from a memory having a variable content.
12. A circuit for obtaining a state of readiness of an oxygen measurement sensor, comprising
    a microcomputer and a switch controllable by the microcomputer;
    a first resistor, said oxygen measurement sensor, and a series circuit of a second resistor and said switch being connected in parallel; and
    an analog-to-digital converter associated with the microcomputer, an input terminal of the converter being connected to the oxygen measurement sensor.
13. The circuit according to claim 12, further comprising
    an impedance transformer connected between the oxygen measurement sensor and the input of the analog-to-digital converter.
14. The circuit according to claim 13, wherein the controllable switch comprises a transistor.

* * * * *